US008465633B2

(12) United States Patent
De Sanoit et al.

(10) Patent No.: US 8,465,633 B2
(45) Date of Patent: Jun. 18, 2013

(54) PROCESS FOR ACTIVATING A DIAMOND-BASED ELECTRODE, ELECTRODE THUS OBTAINED AND USES THEREOF

(75) Inventors: Jacques De Sanoit, Rungis (FR); Emilie Vanhove, Gif sur Yvette (FR)

(73) Assignee: Commissariat a l'Energie Atomique, Paris (FR)

( * ) Notice: Subject to any disclaimer, the term of this patent is extended or adjusted under 35 U.S.C. 154(b) by 641 days.

(21) Appl. No.: 12/602,345

(22) PCT Filed: Jun. 5, 2008

(86) PCT No.: PCT/EP2008/057032
§ 371 (c)(1),
(2), (4) Date: May 20, 2010

(87) PCT Pub. No.: WO2008/148861
PCT Pub. Date: Dec. 11, 2008

(65) Prior Publication Data
US 2011/0108433 A1  May 12, 2011

(30) Foreign Application Priority Data
Jun. 5, 2007 (FR) ..................... 07 55485

(51) Int. Cl.
*C25B 11/12* (2006.01)
*C25B 11/04* (2006.01)
*C25B 11/00* (2006.01)

(52) U.S. Cl.
USPC ........................ 204/294; 204/280; 204/291

(58) Field of Classification Search
USPC ........................... 204/280, 291, 294
See application file for complete search history.

(56) References Cited

U.S. PATENT DOCUMENTS
2006/0175953 A1  8/2006 Swain et al.

FOREIGN PATENT DOCUMENTS
WO  WO 01/25508 A1  4/2001

OTHER PUBLICATIONS

Mahe et al, Electrochemical reactivity at graphitic micro-domains on polycrystalline boron doped diamon thin-film electrodes, Electrochimica Acta 50 (2005) 2263-2277.*
Mahe et al., "Electrochemical Reactivity at Graphitic Micro-Domains on Polycrystalline Boron Doped Diamond Thin-Films Electrodes", Electrochimica Acta, vol. 50, No. 11, Apr. 2005, pp. 2263-2277.
Beck et al., "Boron doped diamond/titanium composite electrodes for electrochemical gas generation from aqueous electrolytes", Electrochimica Acta, vol. 44, No. 2-3, Sep. 1998, pp. 525-532.
Rao et al., "Recent Advances in Electrochemistry of Diamond", Diamond and Related Materials, vol. 9, No. 3-6, Apr. 2000, pp. 384-389.
Becker et al., "The Impedance of Fast Charge Transfer Reactions on Boron Doped Diamond Electrodes", Electrochimica Acta, vol. 49, 2003, pp. 29-39.

(Continued)

*Primary Examiner* — Keith Hendricks
*Assistant Examiner* — Salil Jain
(74) *Attorney, Agent, or Firm* — Miles & Stockbridge P.C.

(57) ABSTRACT

The present invention relates to a process for activating a diamond-based electrode, which includes a step consisting in subjecting, in the presence of an aqueous solution containing an ionic electrolyte, said electrode to an alternately cathodic and anodic polarization potential, of increasing amplitude so as to obtain an anodic and cathodic current density of between $10\,\mu A/cm^2$ and $1\,mA/cm^2$. The present invention also relates to a diamond-based electrode activated by said process and to the uses thereof.

14 Claims, 9 Drawing Sheets

OTHER PUBLICATIONS

Juttner et al., "Characterization of Boron-Doped Diamond Electrodes by Electrochemical Impedance Spectroscopy", Journal of Applied Electrochemistry, vol. 37, 2007, pp. 27-32.

Ferro et al., Electrochemistry of the Aqueous Ceric/Cerous Redox Couple at Conductive Diamond and Gold Electrodes, Phys. Chem. Phys., vol. 4, 2002, pp. 1915-1920.

Granger et al., "The Influence of Surface Interactions on the Reversibility of Ferri/Ferrocyanide at Boron-Doped Diamond Thin-Film Electrodes", Journal of the Electrochemical Society, vol. 146, No. 12, 1999, pp. 4551-4558.

Girard et al., "Effect of Anodic and Cathodic Treatments on the Charge Transfer of Boron Doped Diamond Electrodes", Diamond and Related Materials, vol. 16, 2007, pp. 316-325.

Goeting et al., "Electrochemically Induced Surface Modifications of Boron-Doped Diamond Electrodes: an X-ray Photoelectron Spectroscopy Study", Diamond and Related Materials, vol. 9, 2000, pp. 390-396.

Hupert et al., "Conductive Diamond Thin-Films in Electrochemistry", Diamond and Related Materials, vol. 12, 2003, pp. 1940-1949.

Tryk et al., "Relationships Between Surface Character and Electrochemical Processes on Diamond Electrodes: Dual Roles of Surface Termination and Near-Surface Hydrogen", Diamond and Related Materials, vol. 10, 2001, pp. 1804-1809.

Yagi et al., "Electrochemical Selectivity for Redox Systems at Oxygen-Terminated Diamond Electrodes", Journal of Electroanalytical Chemistry, vol. 473, 1999, pp. 173-178.

* cited by examiner

PROCESS FOR ACTIVATING A DIAMOND-BASED ELECTRODE, ELECTRODE THUS OBTAINED AND USES THEREOF

TECHNICAL FIELD

The present invention falls within the field of diamond-based electrodes, their preparation and their activation.

More particularly, the present invention relates to a method of treating a diamond-based electrode capable of producing, by electrochemical activation, electrodes having a high electrochemical reactivity, which is stable over time, and to the use thereof.

PRIOR ART

Diamond, a crystal consisting of tetrahedral arrangements of carbon atoms of sp3 type, has remarkable properties. The attributes of this material, such as for example its extreme hardness, its corrosion resistance, its wide-forbidden band semiconductive character, its bio-inertness and its thermal conductivity, mean that it is being increasingly used in fields as varied as optics, electronics, health, energy or even mechanical engineering. However, the shortage, and consequently the prohibitive cost, of natural diamond has for a long time inhibited the growth of its applications, despite its promising attributes. The development of innovative high-pressure high-temperature synthesis processes, and more recently low-pressure low-temperature processes such as chemical vapour deposition, has over the last fifteen or so years, led to a growth in its applications.

Efficient techniques have been developed for economically growing polycrystalline diamond films on substrates that are less expensive than diamond. In addition, these methods allow the incorporation of atoms or molecules such as boron into diamond. In the latter case, a p-type semiconductor is created. In particular, a new type of material for producing electrodes may thus be obtained, called B-NCD (boron-doped nanocrystalline diamond), combining the unique properties of diamond with exceptional electrochemical properties [Hupert et al., 2003].

Electrodes based on boron-doped diamond have advantageous electrochemical properties which include a wide potential window, a stability in aqueous and organic media, low residual currents and a high chemical and electrochemical corrosion resistance [Hupert et al., 2003]. These characteristics make diamond a material of choice for a wide raft of electrochemical applications. Polycrystalline diamond films may be doped to levels inducing behaviour ranging from semiconductive behaviour ($10^{18}<[B]<10^{20}$ cm$^{-3}$) to quasi-metallic behaviour ($[B]>3\times10^{20}$ cm$^{-3}$).

Although semiconductor electrodes are particularly suitable for the purposes of detection or analysis, applications such as electrochemical synthesis, electrolytic treatment of wastewater or bioelectronic sensors require electrodes that are highly conductive or even of metallic behaviour. Recent studies have been carried out on the factors that influence the electrochemical reactivity. Among these primary factors are the actual developed surface area, and therefore the roughness of the crystalline film, the level of boron doping, the non-crystalline carbon phases and the termination of the surface of the film, [Hupert et al., 2003]; [Yagi et al., 1999].

As regards the parameter relating to the termination of the surface of the film, many studies have demonstrated the sensitivity of the electrochemical response of electrodes with respect to the chemical composition of the diamond surface. Thus, hydrogenated films exhibit a hydrophobic character, a negative electron affinity associated with a high reactivity [Yagi et al., 1999]; [Girard et al., 2007]; [Tryk et al., 2001]. Since boron-doped nanocrystalline diamond (B-NCD) is produced in a hydrogenated medium (under a hydrogen plasma), the surface of the material leaving the synthesis reactor has a hydrogen termination resulting in a high electrochemical reactivity [Tryk et al., 2001]. Unfortunately, exposure to air for several days or simple use as working electrode results in a large drop in this reactivity. However, this latter tends to stabilize, but at around values that are insufficient for key electrochemical applications. To illustrate this phenomenon, FIG. 1 shows the drop in the electron transfer rate constant ($k_0$) measured on a B-NCD electrode just after having been synthesized, as a function of the chronological succession of experiments.

These experiments were carried out by electrochemical impedance spectroscopy (EIS) using an equimolar solution of a fast redox couple ($Fe(CN)_6^{3-/4-}$) and using the equilibrium potential ($E_0+0.21$ V/SCE). Since an impedance measurement lasts about 5 minutes, it may be seen that the value of $k_0$ passes from $5.9\times10^{-2}$ to $4.2\times10^{-3}$ cm/s after only one hour without being subjected to any potential.

FIG. 2 shows two EIS spectra recorded with two B-NCD working electrodes from the same batch, one before exposure to air for a period of ten days and the other after said exposure. $k_0$ values of $5.8\times10^{-2}$ cm/s (before exposure to air) and $2.0\times10^{-4}$ cm/s (after exposure to air) are deduced from the impedance spectrum data. This perfectly reproducible phenomenon, also observed with other samples, makes it possible to conclude that the reactivity of the initially hydrogenated B-NCD electrodes is greatly degraded after simple exposure to air for a few days.

This decrease in the electrochemical reactivity is rarely mentioned by authors in their publications, but this transpires however through mentioning the detection of oxygen at the surface of the films that are initially hydrogenated and then exposed to air. The need for certain authors to periodically reactivate their electrodes by a hydrogen plasma treatment also reveals this problem. In contrast, oxidized surfaces are stable, hydrophilic, possess a positive electron affinity, but also have a lower reactivity [Yagi et al., 1999]; [Girard et al., 2007]; [Tryk et al., 2001].

Various surface treatments aimed at modifying the surface termination of B-NCD and thus optimizing the electrochemical properties thereof have already been proposed for solving such a technical problem. Specifically, among the abundant surface treatments in the specialized literature are the following: heat treatments [Ferro et al., 2002]; plasma treatments [Goeting et al. 2000]; photochemical treatments, singlet oxygen, ozone and chemical oxidation (hot $KNO_3/H_2SO_4$) treatments and finally electrochemical treatments. The latter treatments usually consist in imposing a fixed potential for a defined time by anodic polarization in an $HClO_4$ medium [Ferro et al., 2002], in an $HNO_3$ medium or in an $H_2SO_4$ medium [Girard et al., 2007], by cathodic polarization or else in applying a cyclic potential variation in the anodic or cathodic range starting from an equilibrium potential (cycling between 0 and +2.5 V/SEC in a phosphate buffer solution at pH 2 [Goeting et al., 2000]. The increase in performance stability of oxygenated diamond materials does not, however, mean that their modest electrochemical reactivity can be forgotten.

Becker and Jüttner [Becker and Jüttner, 2003 and 2007] have pretreated their B-NCD electrodes by carrying out 100 redox cycles in an $Na_2SO_4$ solution in the decomposition zone of the aqueous solvent. However, Becker and Jüttner do not describe in detail the protocol used: they provide no indication about the potential window, the current density or the scan speed used. It is not possible for a person skilled in the art to reproduce the pretreatment or to evaluate the desired or achieved advantage of this pretreatment, since the electrochemical characteristics of the specimen were not measured before said pretreatment. This publication is therefore not conclusive.

Despite the profusion of studies, the mechanisms linking the electrochemical treatments, the surface state and the electrochemical properties remain poorly understood. The studies carried out lead to results that are dependent on the reaction mechanism for a particular redox couple and that often turn out to be contradictory. Thus, as an illustration, Ferro and his co-workers, who have studied the effect of the nature of the surface terminations on the charge transfer of electrodes based on boron-doped diamond, have not observed a significant variation in the $\Delta E_p$ values of cyclic voltammetry curves with oxidized electrodes using the $Ce^{4+/3+}$ redox couple [Ferro et al., 2002]. These authors confirm a metallic behaviour of their highly-doped electrodes. The work presented by Girard and his co-workers under very similar conditions has established a different behaviour and an appreciable decline in the charge transfer rate after a moderate anodic treatment (100 $\mu$A cm$^{-2}$ for 10 s) [Girard et al., 2007].

In the literature, the effect of oxidizing the surface on the charge transfer between the surface of the electrode and the fast redox couple $Fe(CN)_6^{3-/4-}$ is also highly controversial. In the case of Yagi and Girard [Yagi et al., 1999]; [Girard et al., 2007], the system is more irreversible after a moderate electrochemical treatment or an oxygen plasma treatment. Granger and his co-workers [Granger et al., 1999] have explained that the reaction seems to take place via a specific oxygen-inhibited surface site. In contrast, other authors have demonstrated an improvement in the charge transfer rate by anodizing the electrodes [Goeting et al., 2000].

There is therefore a real need to obtain electrodes based on borated diamond and, more generally, electrodes based on doped or undoped diamond, having improved properties in terms of charge transfer rate, stability and/or reproducibility of the electrochemical properties.

SUMMARY OF THE INVENTION

The present invention makes it possible to solve the above-mentioned technical problems by providing a particular electrochemical treatment capable of producing diamond-based electrodes that have a high electrochemical reactivity and are stable over time and their use.

Specifically, the studies on which the present invention is based relate to the potential window (or potential frame) that constitutes an essential characteristic of a diamond-based electrode. This feature characterizes the potential range in which the electrode can be used without any electrolytic decomposition of the aqueous solvent being observed, said solvent containing a non-electroactive salt (oxidation of water in the anodic range with production of gaseous oxygen, and reduction of water in the cathodic range with production of gaseous hydrogen). In general, within the context of B-NCD electrodes, the width of the potential window in aqueous medium lies between 3 and 3.5 V, this value possibly varying, especially as a function of the level of doping of the diamond and the surface termination, and being determined for an anodic and cathodic current density of ±50 $\mu$A/cm$^2$.

The determination of the potential window is therefore an important step in the characterization of a diamond-based electrode and especially a B-NCD electrode. It is carried out during a potential scan in an advantageously deaerated support electrolyte containing a non-electroactive base salt present in macroconcentration (for example, for a B-NCD electrode, LiClO$_4$ with a concentration of 0.5 mol/l). The deaeration is carried out by argon bubbling through the electrolyte for at least 15 minutes before use. The experiment for determining the potential window starts by progressively increasing limits of the potential range. In the case of a B-NCD electrode, this increase is carried out until anodic and cathodic currents of the order of ±150 $\mu$A/cm$^2$ are obtained and the potential window of the electrode is equal (by convention) to the potential range corresponding to a current density of ±50 $\mu$A/cm$^2$. FIG. 3 shows a typical voltammogram used for determining a potential window with a B-NCD electrode.

Incidentally, the inventors have observed that the fact of alternately polarizing, for high potential values possibly ranging up to ±1.8 V (Ag/AgCl, [KCl]=3M), a B-NCD electrode in deaerated aqueous medium containing a non-electroactive salt considerably improves its electrochemical properties and its long-term stability. This phenomenon will be referred to hereafter as "redox activation".

Although deriving from a conventional characterization experiment, redox activation is quite a novel method of activating B-NCD electrodes and in general any diamond-based electrode. This is because the potential window is always measured after the other characterizations (cyclic voltammetry, EIS, etc.), as this operation may sometimes prove to be damaging or even destructive for the material under test. Moreover, very high current densities may accidentally pass through the tested electrodes during an increase in weak potentials (vertical rise in the $J(\mu A/cm^2)=f(E(V))$ curves) at the potential window limits.

In addition, to try to activate a diamond-based electrode by redox cycling is an intellectually counter-intuitive approach. This is because it might be expected that the surface terminations caused by anodic activation would be modified, or even destroyed, during the scan in the cathodic range, and vice versa. However, the experiments have shown a different behaviour.

Therefore, the present invention relates to a process for activating a diamond-based electrode, which includes a step consisting in subjecting, in the presence of an aqueous solution containing an ionic electrolyte, said electrode to an alternately cathodic and anodic polarization potential, of increasing amplitude so as to obtain an anodic and cathodic current density of between 10 $\mu$A/cm$^2$ and 1 mA/cm$^2$.

The expression "activation of an electrode" is understood, within the context of the present invention, to mean the action of subjecting said electrode to a treatment, in this case an electrochemical treatment, capable of improving the properties of the electrode in terms of electrochemical reactivity.

The process of the present invention is noteworthy in that it applies to any type of diamond-based electrode, whether or not the diamond is doped, and, within the context of doped-diamond-based electrodes, to any type of dopant.

Thus, the expression "diamond-based electrode" is understood, within the context of the present invention, to mean any electrode of which the constituent, or one of the constituents, is diamond. Within the context of the present invention, a diamond-based electrode may just as well be an electrode consisting only of diamond as an electrode in which the diamond constitutes merely a portion of said electrode. In this case, the diamond may take the form of a thin film, whether continuous or discontinuous, such as a film on the surface of a substrate, such as a substrate containing Fe, Ti, Zr, Nb, Ni, Ta, Mo, W, B, Si, graphite and/or diamond. As a consequence, the diamond of the electrode used in the present invention may take the form of monocrystalline diamond, macrocrystalline diamond, microcrystalline diamond, nanocrystalline diamond or ultrananocrystalline diamond (UNCD).

In a first variant of the present invention, the diamond of the electrode used is exclusively undoped diamond.

In a second variant, the diamond-based electrode comprises doped diamond. The doped diamond may be at the surface of the electrode. Advantageously, the entire diamond of the electrode is doped diamond. Any dopant, and in particular any bivalent, trivalent or pentavalent dopant, may be used within the context of the present invention. More particularly, the dopant is chosen from the group consisting of boron, nitrogen, phosphorus, nickel, sulphur and mixtures thereof.

A person skilled in the art knows various techniques capable of preparing electrodes based on either doped or undoped diamond, such as those envisaged above. As an example, but not in any way limiting, the technique used may be hot-filament or microwave-plasma chemical vapour deposition of diamond.

Within the context of doped-diamond-based electrodes, a person skilled in the art will know, without involving inventive skill, what amount of dopant or mixture of dopants to use depending on the desired behaviour of the doped (semiconductive or quasi-metallic) diamond and/or depending on the subsequent use of the electrode. To give an example, an electrode based on borated diamond that can be used within the context of the present invention may contain more than $10^{18}$ boron atoms per $cm^3$ and especially more than $10^{20}$ boron atoms per $cm^3$.

Any ionic electrolyte known to those skilled in the art can be used within the context of the present invention. Advantageously, the ionic electrolyte employed is a non-electroactive ionic electrolyte. The expression "non-electroactive ionic electrolyte" is understood, within the context of the present invention, to mean an ionic electrolyte containing a non-electroactive salt in macroconcentration, which, at the potentials employed in the method of the invention, ensures conduction of the electric charges but is not capable of participating in a redox reaction other than the electrochemical decomposition of water. More particularly, the non-electroactive ionic electrolyte is an aqueous solution of a non-electroactive salt. Said non-electroactive salt may especially be chosen from the group consisting of $LiClO_4$, $NaClO_4$, $KClO_4$, $Na_2SO_4$, $K_2SO_4$ and $Li_2SO_4$. The advantageously non-electroactive ionic electrolyte or the non-electroactive ionic salt may be present in the aqueous solution in an amount ranging from 0.01 to the solubility limit of said electrolyte or of said salt. To give an example, an aqueous $LiClO_4$ solution with a concentration ranging from 0.5 to 1M may be used, especially within the context of a borated-diamond-based electrode.

Preferably, the aqueous solution containing an advantageously non-electroactive ionic electrolyte is deaerated before the process of the invention is implemented. This is because the prior deaeration of the aqueous solution makes it possible to avoid, while the process of activation is being carried out, reduction of the oxygen dissolved in the water during the scan in the cathodic range. Any technique known to those skilled in the art enabling an aqueous solution to be deaerated can be used within the context of the present invention. To give an example, this technique may consist of an argon sparging (or bubbling), within the aqueous solution, lasting several minutes and in particular lasting 15 minutes.

The redox activation process according to the present invention consists in progressively increasing, from the equilibrium potential, the potential range until a moderate anodic and cathodic current density is obtained, which is slightly above the anodic or cathodic current density at which the aqueous solution starts to decompose into oxygen and hydrogen. The current density at which the aqueous solution starts to decompose is a parameter that a person skilled in the art can readily appreciate (typically $J=10\ \mu A/cm^2$).

The fact of imposing, during the process for activation of the invention, a low current density limits the production of gas, at the diamond-based electrode, by oxidation and reduction of water, which phenomenon could result in non-uniform modifications of the surface termination. Indeed, the attachment of gas bubbles on the doped or undoped diamond of the electrode would modify its surface area by a screening effect. The reduction in surface area would, as a direct consequence, artificially increase the current density in the unconcealed zones and create dead zones at the points of attachment of the gas bubbles where the electrochemical activation would be blocked until the bubbles are naturally removed during the treatment.

The fact of imposing on the diamond-based electrode, during the method of activation, moderate to low current density is an essential aspect of the present invention. Thus, any process for obtaining such current densities that absolutely avoids any current density which, because of its absolute value being too high, would risk damaging the electrode must be considered as able to be used within the context of the present invention.

Preferably, the process of the invention consists in progressively increasing, from the equilibrium potential, the potential range until an anodic and cathodic current density is obtained which is less than $\pm 1\ mA/cm^2$, namely between $\pm 10$ and $\pm 1000\ \mu A/cm^2$, especially between $\pm 10$ and $\pm 900\ \mu A/cm^2$, in particular between $\pm 10$ and $\pm 800\ \mu A/cm^2$ and more particularly $\pm 10$ and $\pm 700\ \mu A/cm^2$. To give an example and within the context of a borated-diamond-based electrode, the potential to which the electrode is subjected is adjusted so as to obtain equal anodic and cathodic current densities between 10 and 500 $\mu A/cm^2$. Particularly preferred current densities are advantageously between 300 and 500 $\mu A/cm^2$ (for example 400 $\mu A/cm^2$) or between 100 and 200 $\mu A/cm^2$ (for example, 150 $\mu A/cm^2$).

The potential to be applied to the diamond-based electrode in order to obtain such current densities may vary by several tens of mV depending on the nature of the electrode to be activated and depending on the nature of the non-electroactive ionic electrolyte employed and its concentration. A person skilled in the art would know, by measuring the potential of the electrode in an aqueous solution containing the same non-electroactive ionic electrolyte as that employed within the context of the process for activation, how to determine the potential to be applied according to the desired current density. To give an example, and within the context of a borated-diamond-based electrode, the potential to be applied to the electrode in order to obtain a current density in the region of 400 $\mu A/cm^2$ or in the region of 150 $\mu A/cm^2$ lies between $-1.85\pm 0.05$ V and $+1.70\pm 0.05$ V and between $-1.50\pm 0.5$ V and $+1.50\pm 0.5$ V, respectively. These values are expressed here relative to a reference electrode, which is a silver/silver chloride electrode having, as internal electrolyte, a potassium chloride solution of 3 mol/l concentration (said reference electrode being denoted herein by "Ag/AgCl, [KCl]=3M").

In a preferred way of implementing the process according to the invention, the first potential to which the diamond-based electrode is subjected is a cathodic polarization potential. In an alternative preferred way of implementing the process according to the invention, the first potential to which the diamond-based electrode is subjected is an anodic polarization potential. The increasing amplitude of the potential to which the diamond-based electrode is subjected within the framework of the process according to the invention is obtained by means of potential increments, the value of which is advantageously between 50 and 150 mV and especially around 100 mV. To give an example, and within the context of a borated-diamond-based electrode, one correct experimental approach consists in progressively increasing the potential range starting from [−1.5 V; +1.5 V] values using a three-electrode device as defined hereafter by 100 mV increments and then 50 mV increments until the desired current density (J) values are obtained, i.e. an anodic current density of +400 $\mu A/cm^2$ and a cathodic current density of −400 $\mu A/cm^2$. As a variant, the correct experimental approach consists in progressively increasing the potential range from [−1.1 V; +1.1 V] values using a three-electrode device as defined hereafter by 100 mV increments and then 50 mV increments until an anodic current density of +150 $\mu A/cm^2$ and a cathodic current density of −150 $\mu A/cm^2$ are obtained.

Within the context of the process for activation according to the invention, it is important to work, as regards the increasing amplitude potential, by successive approaches so as to preserve the electrode from any impairment in the event of an accidental overvoltage. Without wishing to be tied by any particular theory, it is possible that the absence of an approach by means of increments might explain the inconclusive results of the electrochemical activation employed by Becker and Jüttner [Becker and Jüttner, 2003 and 2007].

The process for activating a diamond-based electrode according to the invention may include a subsequent step consisting, when the desired anodic and cathodic current density is reached, in subjecting the electrode to at least one alternately cathodic and anodic polarization potential cycle of constant amplitude, especially at least two and, in particular, at least three such cycles. It is clear that the constant potential of this step is the potential allowing the desired anodic and cathodic current densities to be achieved. In this subsequent step, the diamond-based electrode is advantageously subjected to more than 5, in particular to more than 10 and most particularly to between 10 and 50 alternately cathodic and anodic polarization potentials of constant amplitude. In principle, there is no benefit in extending this subsequent step of the treatment to beyond 50 cycles.

In a preferred way of implementing the process according to the invention, the final potential to which the diamond-based electrode is subjected is an anodic polarization potential which reaches the equilibrium potential (OCP).

According to the present invention, the alternation between cathodic polarization and anodic polarization for each potential is carried out at a rate of between 50 and 150 mV/s and advantageously equal to 100 mV/s. This scan rate applies both to the step during which the diamond-based electrode is subjected to a potential of increasing amplitude and to the subsequent step during which the potential is of constant amplitude.

As a variant of the continuous procedure defined above, it is conceivable to have a discrete procedure for alternating between cathodic and anodic polarization without a scan, both at the step during which the diamond-based electrode is subjected to a potential of increasing amplitude and the subsequent step during which the potential is of constant amplitude.

In another variant, the continuous procedure and the discrete procedure may be implemented during one and the same process for activation.

The device for implementing the process according to the present invention is what is called a three-electrode arrangement. Specifically, the redox activation experiments are carried out in an electrochemical cell equipped with a reference electrode, a working electrode and a counterelectrode. Any reference electrode may be used. A person skilled in the art knows which reference electrodes are suitable to be used without having to exercise inventive skill. The reference electrode is either of SCE (saturated calomel electrode) type or an Ag/AgCl, [KCl]=3M reference electrode, or optionally a simple platinum wire. The working electrode is the preferably doped diamond electrode, and the counterelectrode is a platinum mesh having a surface area at least five times greater than that of the working electrode. FIG. 5 shows an example of one possible arrangement. A variant of this arrangement may consist in immobilizing the diamond so that it constitutes the bottom of the cell. In this case, the working electrode is no longer of the immersed electrode type. The electrolyte is an aqueous solution containing a non-electroactive ionic electrolyte, such as, for a B-NCD electrode, $LiClO_4$ at 0.5M concentration, without the pH being adjusted beforehand. The various electrodes are connected to a current generator of the potentiostat type. The potential scan is controlled by a PC provided with software for communicating with the potentiostat.

Since the redox activation is a reversible phenomenon, it is possible for an electrode which had, through intensive use in the field of electrochemical measurement (electrode, sensor, etc.), lost all or part of its reactivity to be periodically reactivated by the process according to the invention.

Consequently, the present invention relates to the use of a process as defined above for restoring the electrochemical reactivity of a diamond-based electrode as defined above. In particular, it may be necessary to restore the electrochemical reactivity of a diamond-based electrode that has lost some of its reactivity after being stored in air for a long period or after intensive analytical use in the electrochemistry field.

When the process for activation according to the present invention is being implemented, the voltammograms may vary in intensity and/or in shape. This may be due to the nature of the diamond surface terminations of the electrode being modified. FIG. 5 shows the superposition of a few voltammograms obtained for a given experiment during the redox activation of a B-NCD electrode.

After said redox activation process, the diamond-based electrodes possess excellent reactivity and good stability over time. Surprisingly and characteristically, a given redox activation process of the present invention implemented on electrodes of the same nature makes it possible to obtain activated electrodes having identical properties in terms of electrochemical reactivity, whereas identical non-activated electrodes or electrodes activated by some of the activation processes of the prior art exhibit variable properties. A few examples of the performance obtained for electrodes activated by the process of the invention will be given below.

Therefore, the present invention also relates to an activated diamond-based electrode that can be obtained by an activation process as defined above. This diamond-based electrode has in particular an improvement in electrochemical properties such as the electron transfer rate constant $k_0$ measured with a fast redox couple and the separation of the anodic and cathodic peaks.

The activated diamond-based electrode that can be obtained by a process for activation as described above may have, as major component of the carbon components in an XPS spectrum obtained in 30° configuration (sensitive to the surface), the component $CH_x$ where x is equal to 2 or 3. The expression "carbon components" is understood, within the context of the present invention, to mean the components involving at least one carbon atom, such as the components C—C, CH, $CH_x$ where x is equal to 2 or 3, COH, COC and C=O. The expression "major component" is understood, within the context of the present invention, to mean the carbon component which is the most abundant relative to all the carbon components. A person skilled in the art would know how to obtain, from an XPS spectrum obtained in 30° configuration, the photoemission peaks of each of the carbon components and especially those listed above and, for each peak, its area, which is proportional to the abundance of the binding state of the carbon in question. It has been observed that, for certain electrodes based on activated hydrogenated diamond that can be obtained by an activation process as defined above, the ratio of the $CH_x$ component, where x is equal to 2 or 3, to the sum of the carbon components is greater than the ratio obtained for the same, but not activated, electrode by a factor of at least 1.2, especially at least 1.4, in particular at least 1.6 and most particularly at least 1.8.

The activated diamond-based electrode that can be obtained by a process of activation as defined above has an electron transfer rate constant $k_0$, measured using a fast redox couple, greater than the electron transfer rate constant $k_0$ of the same, but not activated, electrode by a factor of at least 1.1, especially at least 2, advantageously at least 5, in particular at least 10, more particularly at least 50 and most particularly at least 100, and may maintain an increased constant especially relative to the observed values before activation, for several weeks of storage in air. According to the present invention, the expression "several weeks" is understood to mean at least two weeks, especially at least four weeks, in particular at least eight weeks and most particularly at least twelve weeks. As a characteristic and important fact, this increased electron transfer rate constant $k_0$, measured using a fast redox couple after activation according to the process of the present invention, is maintained over several electrochemical operating cycles. According to the present invention, the expression "several electrochemical operating cycles" is understood to mean at least four voltammetry cycles, especially at least ten voltammetry cycles, in particular at least 25 voltammetry cycles, more particularly at least 50 voltammetry cycles and most particularly at least 100 voltammetry cycles.

To give an example, a first type of hydrogen-terminated boron-doped electrode activated by the method according to the present invention has its reactivity (the constant $k_0$) increased by a factor of 100 while a second type has its reactivity (the constant $k_0$) increased by a factor of 15-20, 70% of this reactivity being preserved over eight hours of successive electrochemical impedance measurements or after 50 cyclic voltammetry cycles.

On oxidized boron-doped electrodes activated by the process according to the invention, the $k_0$ values are maintained for at least eight hours, i.e. over 30 successive electrochemical impedance measurements (with a maximum observed loss of less than 3%).

The notion of "fast redox couples" is well known to those skilled in the art. As a reminder, certain redox couples, called "fast" redox couples, are characterized by a reversible electrochemical reaction, whereas other redox couples are referred to as "slow" couples as they are characterized by an irreversible electrochemical reaction. Within the context of fast redox couples, the electron exchange with the working electrode is immediate with no modification to the solvation sphere of the species, whereas electron transfer in the case of slow redox couples involves the internal coordination sphere with breaking or formation of intramolecular bonds. This type of reaction is, in addition, often complicated by the adsorption of reactants and/or of reaction products on the surface of the electrode. Within the context of the present invention, the fast redox couples that can be employed are, for example, $Fe(CN)_6^{3-/4-}$, $IrCl_6^{2-/3-}$ or $Ru(NH_3)_6^{2+/3+}$.

To give an example, and within the context of a borated-diamond-based electrode, the process for activation of the invention makes it possible to obtain electron transfer rate constants ($k_0$) greater than $10^{-3}$ cm/s, especially greater than $10^{-2}$ cm/s and in particular greater than 0.2 cm/s for fast redox couples.

In addition, an activated diamond-based electrode according to the present invention has better separation of the anodic and cathodic peaks on a voltammogram ($\Delta E_p$) compared with the separation of the anodic and cathodic peaks for the same, but not activated, electrode. To give an example, and within the context of a borated-diamond-based electrode, the separation of the anodic and cathodic peaks may be reduced to 75 mV, especially 65 mV and in particular 61±2 mV, i.e. close to the theoretical limit of 58-60 mV obtained for a redox couple exchanging a single electron.

The present invention also relates to the use of an activated diamond-based electrode according to the present invention for electrochemical analysis, for detecting trace elements, as electrode in biotechnological detectors and/or in grafting applications.

Finally, the present invention relates to the use of an activated diamond-based electrode according to the present invention for decontaminating the effluents from the chemical, metallurgical or agri-food industries or municipal water.

Other features and advantages of the present invention will also become apparent on reading the examples given below by way of illustration, but implying no limitation, with reference to the appended FIGS. 5 to 15.

DETAILED DESCRIPTION OF PARTICULAR EMBODIMENTS

I. Examples of Electrochemical Activation According to the Invention

I.1. Electrode #272.

Electrode #272 consists of a diamond with predominantly (111) faces (with a surface area of 0.6 cm$^2$) deposited on silicon (Si thickness=350 μm) on which boron-doped diamond was grown (with a thickness of 3.75 10$^{-2}$ μm) in order to render it electroactive on the surface.

Figure 1:
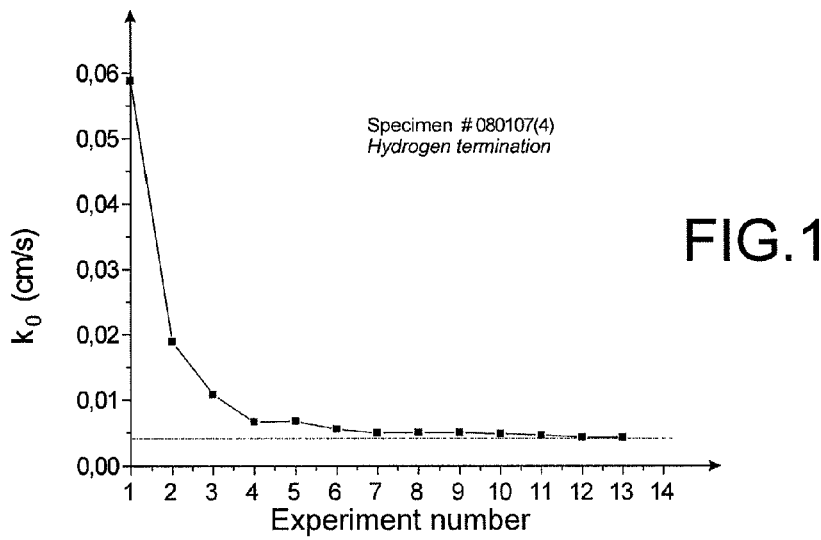
FIG. 1 shows the variation in $k_0$ (in cm/s) over 13 successive EIS experiments ($[Fe(CN)_6^{3-/4-}]=10^{-3}$M, [KCl]=0.5M, $E_0$=0.21 V/SCE).
Figure 2:
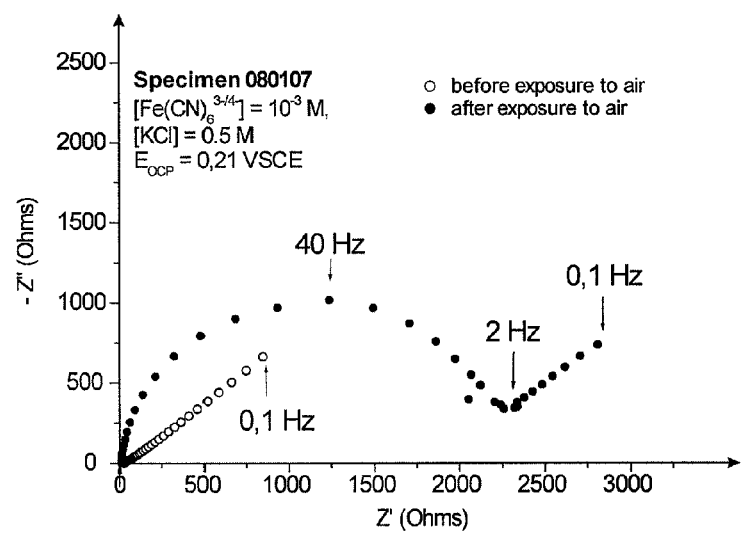
FIG. 2 shows the change in the EIS spectra ($[Fe(CN)_6^{3-/4-}]=10^{-3}$M, [KCl]=0.5M, $E_0$=0.21 V/SCE) over the course of ageing in air for 10 days of an initially hydrogenated electrode.
Figure 3:
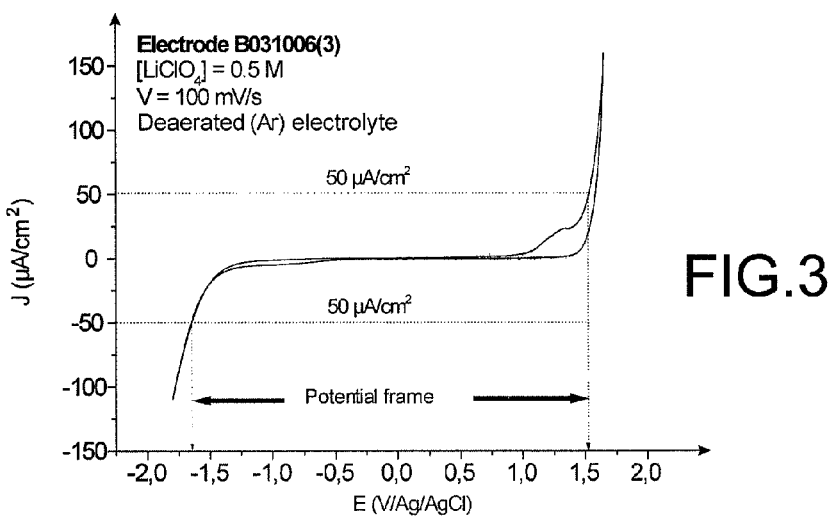
FIG. 3 shows the determination of the potential window of a B-NCD electrode.
Figure 4:
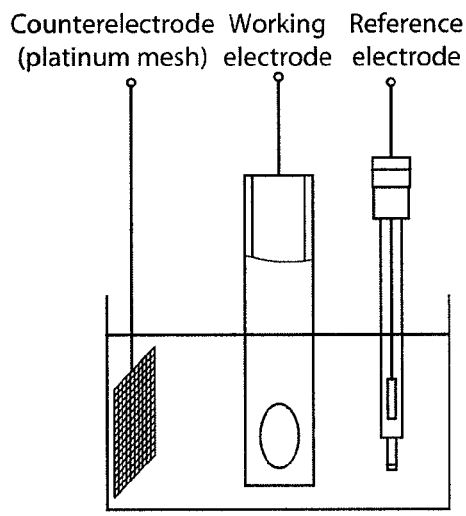
FIG. 4 shows an experimental arrangement used during the redox activation of B-NCD electrodes.
Figure 5:
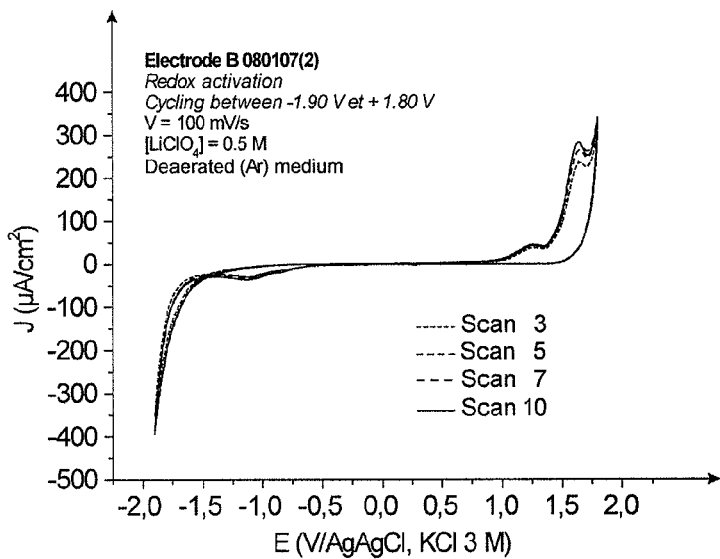
FIG. 5 shows voltammograms for the redox activation of a B-NCD electrode in a 0.5M [$LiClO_4$] medium.
Figure 6A:
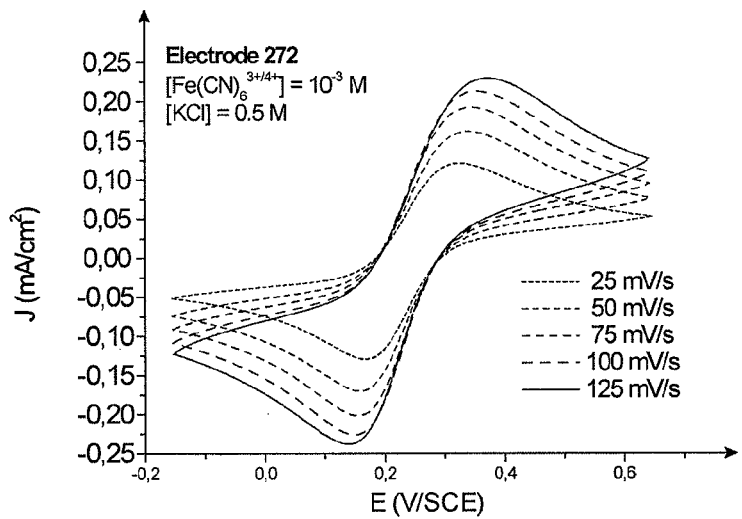
FIG. 6a shows the cyclic voltammetry of electrode #272 as defined hereafter before its redox activation.
Figure 6B:
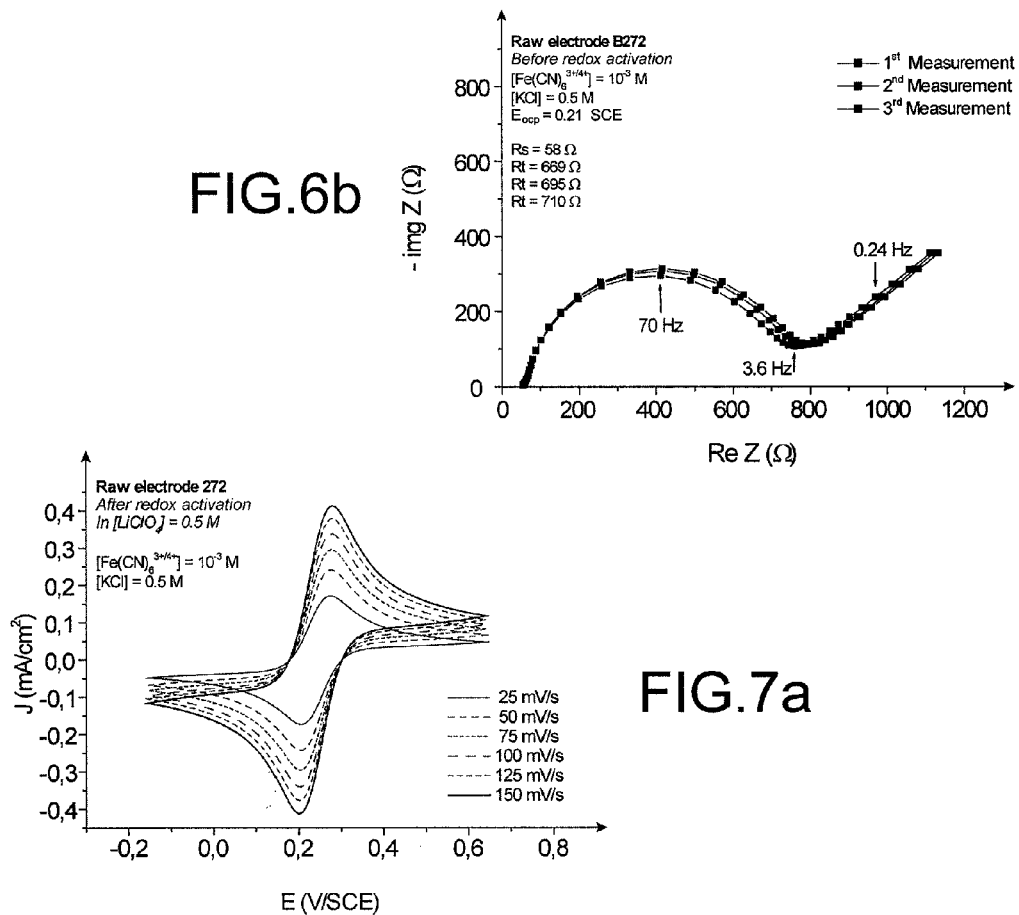
FIG. 6b shows the electrochemical impedance spectroscopy (EIS) of electrode #272 before its redox activation.
Figure 7A:
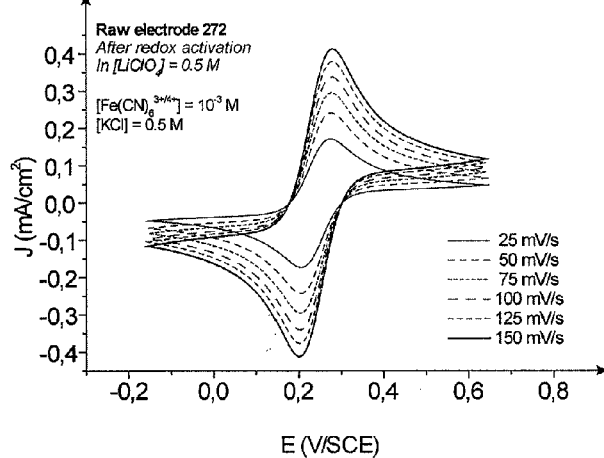
FIG. 7a shows the cyclic voltammetry of electrode #272 after its redox activation.
Figure 7B:
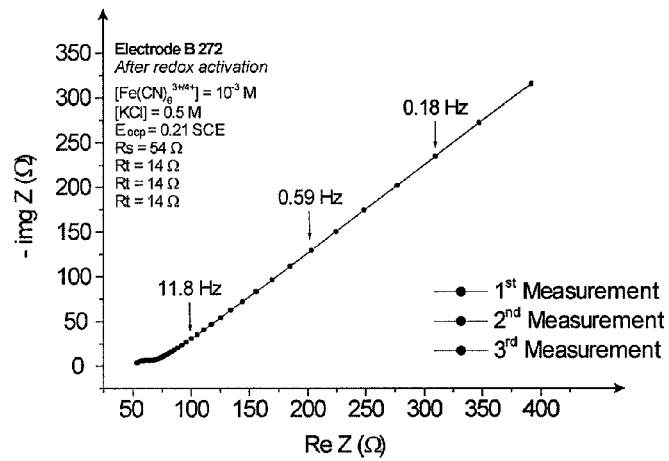
FIG. 7b shows the electrochemical impedance spectroscopy (EIS) of electrode #272 after its redox activation.

Before redox activation, the initial reactivity of the electrode was mediocre. The cyclic voltammetry curves (corrected for ohmic drop) show a large separation ($\Delta E_p$) between the anodic and cathodic peaks. To give an example, with a scan rate of 50 mV/s, we obtained $\Delta E_p$=180 mV (with an ideally reactive electrode, we would obtain, under the same experimental conditions, a $\Delta E_p$~60 mV). This $\Delta E_p$ value increases with scan rate (FIG. 6a), this being an additional argument to explain this lack of reactivity. The impedance spectroscopy (FIG. 6b) shows a high electron transfer resistance ($R_t$~700Ω) resulting in a low electron transfer rate constant $k_0$~6.5×10$^{-4}$ cm/s. After redox activation (potential increase incrementally followed by ten cycles between −1.7 and +1.7 V (Ag/AgCl, [KCl]=3M)), the electrochemical characteristics of the electrode were considerably improved. The cyclic voltammetry curves (FIG. 7a) show a separation of the anodic and cathodic peaks ($\Delta E_p$) of 68 mV. Contrary to what was observed prior to the redox activation, this separation no longer depends on the scan rate. The impedance spectroscopy (FIG. 7b) shows a low electron transfer resistance ($R_t$~14Ω) resulting in a high electron transfer rate constant $k_0$~3.2×10$^{-2}$ cm/s. The reactivity of the electrode has been increased by a factor of 50 and is stable over time.

I.2. Electrode #080107(3).

Electrode #080107(3) consisted of a boron-doped diamond film with an area of 0.60 cm$^2$ and a thickness of 0.530 μm, deposited on a doped silicon substrate. After growth, the specimen was cooled for two hours in a hydrogen atmosphere. Between preparing the specimen and using it, the diamond was exposed to air for some ten days.

Figure 8A:
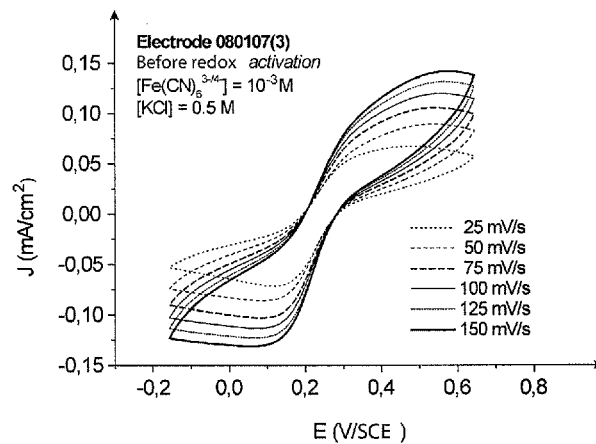
FIG. 8a shows the cyclic voltammetry of electrode #080107(3) before its redox activation.
Figure 8B:
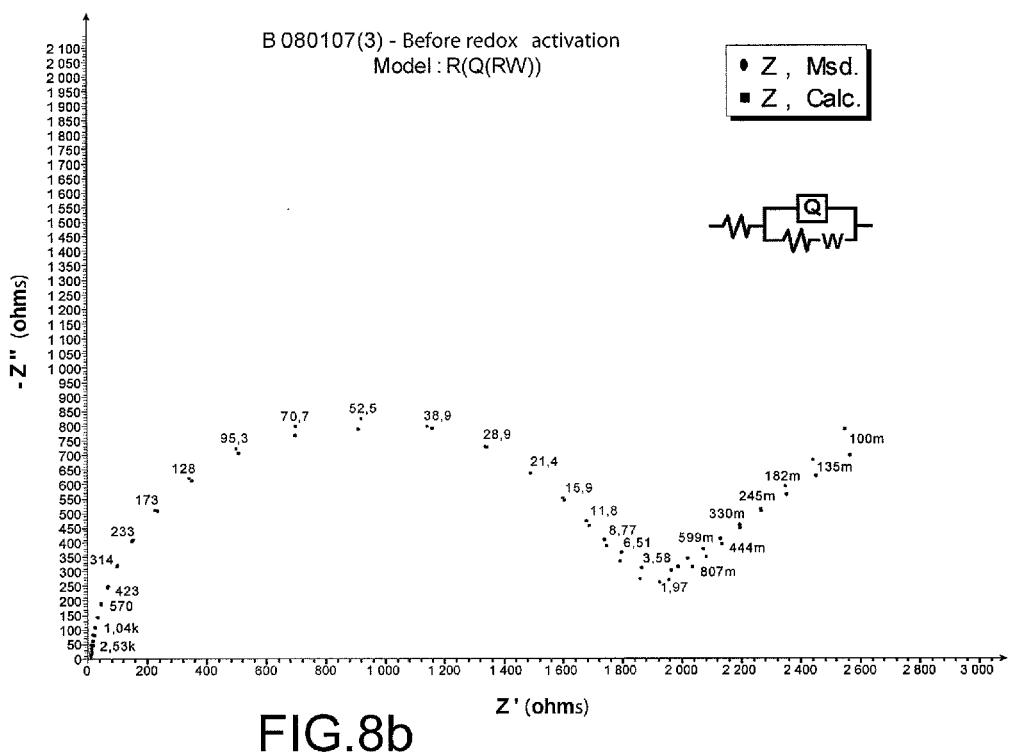
FIG. 8b shows the electrochemical impedance spectroscopy (EIS) of electrode #080107(3) before its redox activation.

Before redox activation, the initial reactivity of the electrode was very mediocre. The cyclic voltammetry curves (FIG. 8a) do not allow the anodic and cathodic peaks to be precisely distinguished, which peaks seem however to be shifted with the scan rate. The current densities were markedly lower than for other specimens tested. The impedance spectroscopy (FIG. 8b) shows a very high electron transfer resistance ($R_t$~1750Ω) resulting in a low electron transfer rate constant $k_0$~2.4×10$^{-4}$ cm/s.

Figure 9A:
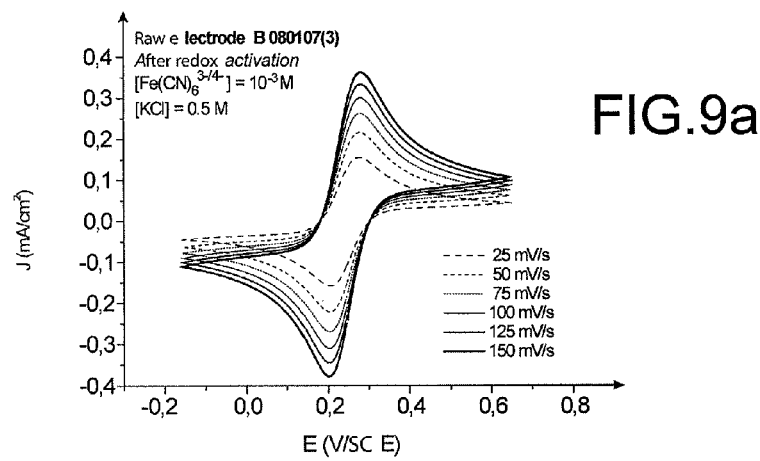
FIG. 9a shows the cyclic voltammetry of electrode #080107(3) after its redox activation.
Figure 9B:
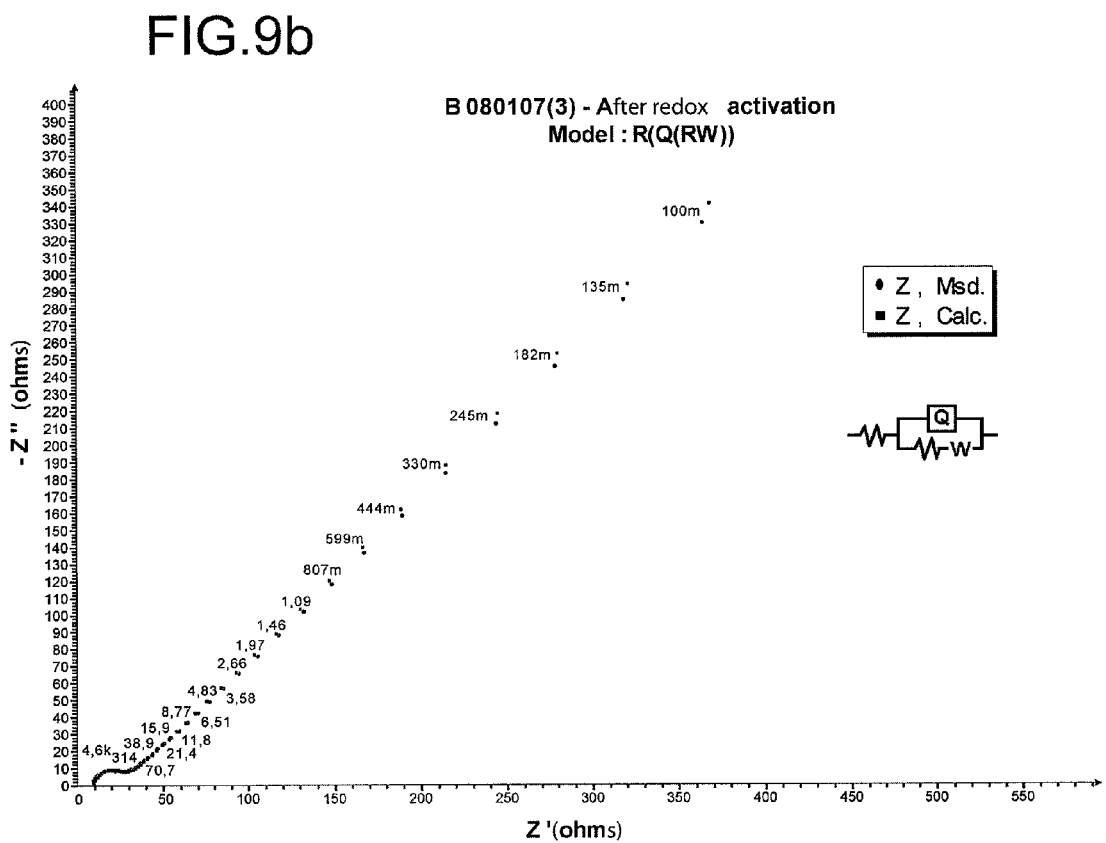
FIG. 9b shows the electrochemical impedance spectroscopy (EIS) of electrode #080107(3) after its redox activation.

After 30 redox activation cycles between −1.75 and +1.70 V (Ag/AgCl, [KCl]=3M), the electrochemical characteristics of the electrode were considerably improved. The cyclic voltammetry curves (FIG. 9a) show higher anodic and cathodic current densities and an anodic/cathodic peak separation ($\Delta E_p$) of 71 mV. Contrary to what was observed before redox activation, this value no longer depended on the scan rate. The impedance spectroscopy (FIG. 9b) shows a low electron transfer resistance ($R_t$~18Ω) resulting in a high electron transfer rate constant $k_0$~2.4×10$^{-2}$ cm/s. The reactivity of the electrode was increased by a factor of 100 and was stable over time.

I.3. Summary of the Data for the Redox Activation Employed in Sections 1.1. and 1.2.

Table 1 below summarizes the redox activation data of electrodes #272 and #080107(3).

TABLE 1

| | Before redox activation | | After redox activation | |
|---|---|---|---|---|
| | $k_0$ (cm/s) | $\Delta E_p$ (mV) (50 mV/s) | $k_0$ (cm/s) | $\Delta E_p$ (mV) (50 mV/s) |
| First example Electrode # 272 | (6.5 ± 0.5) × 10$^{-4}$ | 180 | (3.2 ± 0.3) × 10$^{-2}$ | 68 |
| Second example Electrode # 080107(3) | (2.4 ± 0.2) × 10$^{-4}$ | ~400 | (2.4 ± 0.2) × 10$^{-2}$ | 71 |

II. A Few Examples of Stability After Redox Activation

Table 2 below shows examples of the stability of B-NCD electrodes activated beforehand according to the process described in the invention. The stability was determined by measuring the electron transfer rate constant $k_0$ (in cm/s) before and after 50 redox cycles in electrolytes containing different fast redox couples.

TABLE 2

| Electrode | Redox couple | $\Delta E_p$ (mV) | $k_0$ (in cm/s) before 50 voltammetry cycles | $k_0$ (in cm/s) after 50 voltammetry cycles |
|---|---|---|---|---|
| # 0107-a | IrCl$_6^{2-/3-}$ | 74 | (3.6 ± 0.3) × 10$^{-2}$ | (2.4 ± 0.2) × 10$^{-2}$ |
| # 0107-b | Ru(NH$_3$)$_6^{2+/3+}$ | 78 | (2.1 ± 0.2) × 10$^{-2}$ | (2.0 ± 0.2) × 10$^{-2}$ |
| # 0107-c | Fe(CN)$_6^{3-/4-}$ | 68 | (2.5 ± 0.2) × 10$^{-2}$ | (2.4 ± 0.2) × 10$^{-2}$ |
| # 0107-d | Fe(CN)$_6^{3-/4-}$ | 66 | (7.5 ± 0.7) × 10$^{-2}$ | (6.7 ± 0.7) × 10$^{-2}$ |

III. XPS Analysis of Electrode #080107 Before and After Redox Activation According to the Invention Electrode #080107 was characterized by X-ray photoelectron spectroscopy (XPS) before and after an electrochemical activation treatment according to the invention. Two configurations were used: 0° and 30°. The 0° configuration is referred to as the "standard" configuration, whereas the 30° configuration is much more sensitive to the surface (only the very first atomic layers are probed).

III.1. XPS Analysis before Redox Activation

Figure 10A:
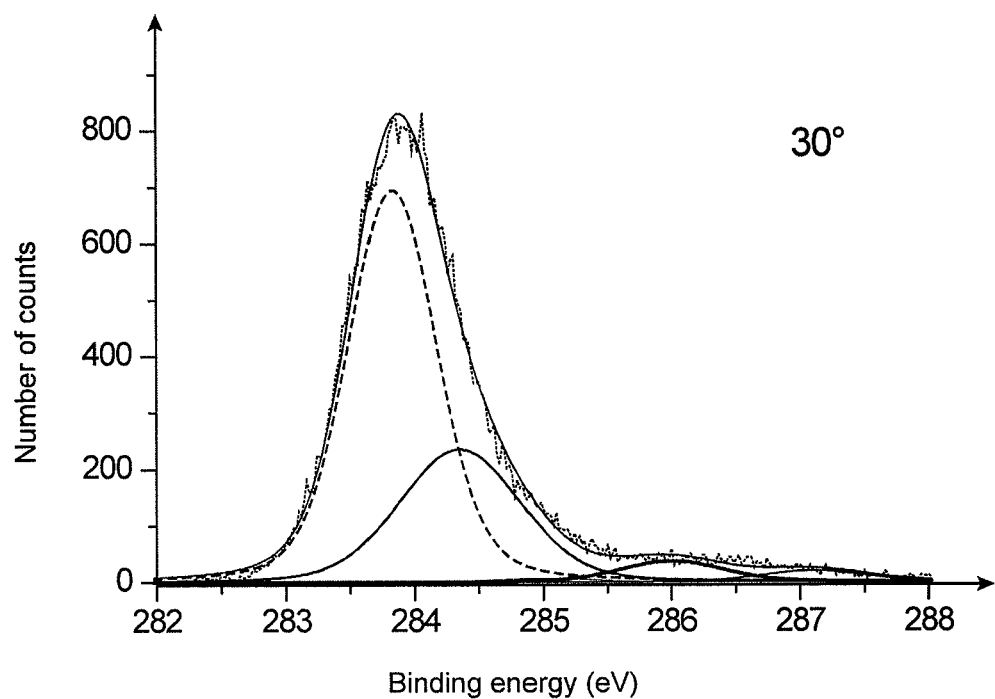
FIGS. 10a and 10b show the XPS spectrum of electrode #080107(3) before its redox activation, in 30° configuration (FIG. 10a) and in 0° configuration (FIG. 10b).
Figure 10B:
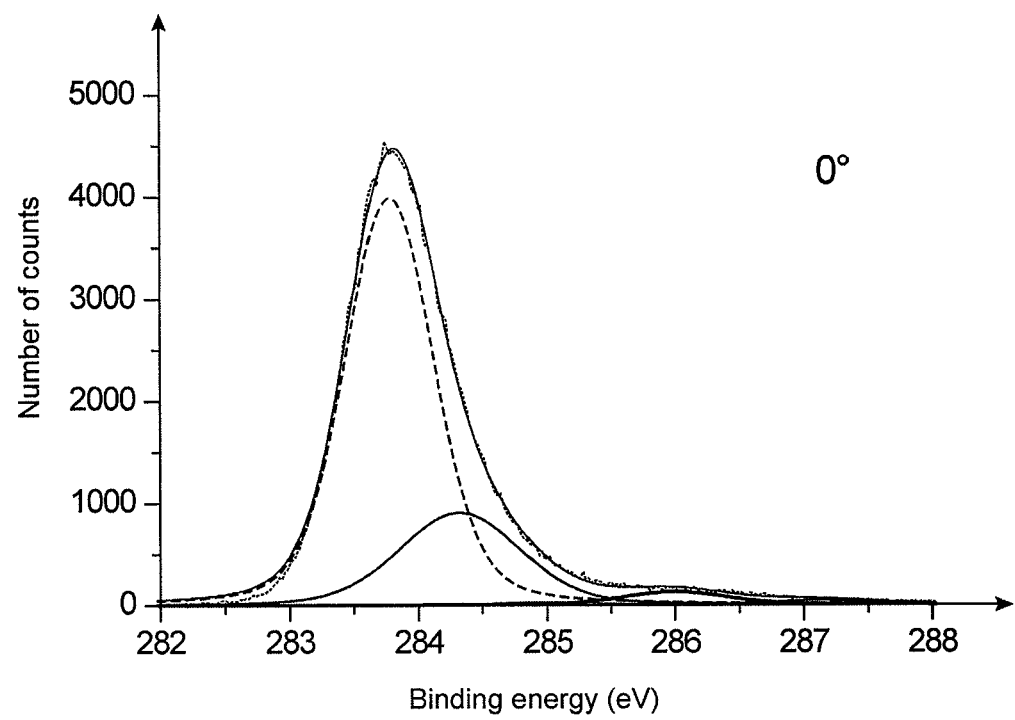

The XPS spectrum obtained for electrode #080107 before its redox activation is shown in FIGS. 10a and 10b in 30° and 0° configurations respectively. The values obtained for each characteristic photoemission peak in these spectra are given in Table 3 below.

TABLE 3

| | Carbon core level B 080701-4 zone 1 | | | | |
|---|---|---|---|---|---|
| Component | 283.8 eV | 284.3 eV | 285 eV | 286 eV | 287.1 eV |
| Assignment | C—C sp3 and CH | $CH_x$ | C—OH | C—O—C | C=O |
| Total 0° area % | 73 | 22 | 1 | 3 | 1 |
| Component | 283.8 eV | 284.3 eV | 285 eV | 286 eV | 287.2 eV |
| Total 30° area % | 64 | 29 | 1 | 4 | 2 |

The results obtained on the various zones are homogeneous. The CHx component represents 22% of the total carbon area in the standard (0°) geometry and 29% in the 30° configuration.

It should be noted that a few components corresponding to various carbon-oxygen bonds are present. The area represented by these components is 8% of the total area of carbon (the average over four zones in the standard geometry).

III.2. XPS Analysis after Redox Activation

Figure 11A:
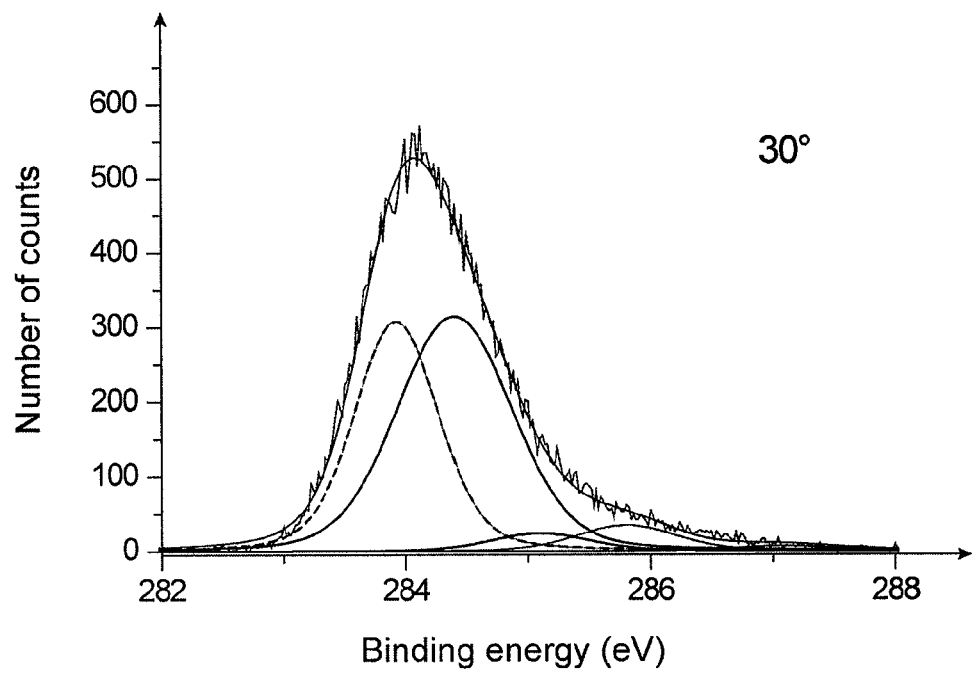
FIGS. 11a and 11b show the XPS spectrum of electrode #080107(3) after its redox activation, in 30° configuration (FIG. 11a) and in 0° configuration (FIG. 11b).
Figure 11B:
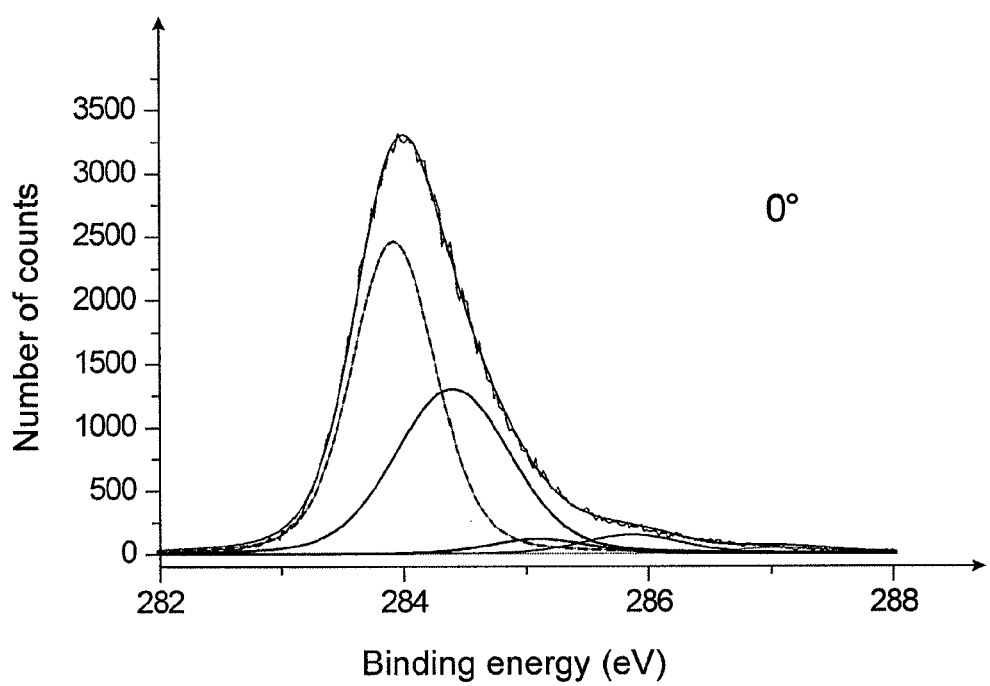

The XPS spectrum obtained for electrode #080107 after its redox activation is shown in FIGS. 11a and 11b in 30° and 0° configuration respectively. The values obtained for each characteristic photoemission peak in these spectra are given in Table 4 below.

TABLE 4

| | Carbon core level B 080701-4 zone 6 | | | | |
|---|---|---|---|---|---|
| Component | 283.9 eV | 284.4 eV | 285.1 eV | 285.8 eV | 287.1 eV |
| Assignment | C—C sp3 and CH | $CH_x$ | C—OH | C—O—C | C=O |
| Total 0° area % | 54 | 38 | 3 | 4 | 1 |
| Component | 283.9 eV | 284.4 eV | 285.1 eV | 285.8 eV | 287.1 eV |
| Total 30° area % | 38 | 52 | 4 | 5 | 1 |

The electrochemical treatment according to the invention consequently enhances the CHx component in the surface-sensitive configuration, said component being much more intense than on the specimen before treatment. The results are very uniform over the four zones observed.

IV. Electrodes B140408(X)

IV.1. Their Redox Activation According to the Process of the Invention.

Electrodes B140408(X) were obtained from a batch of identical diamond specimens (batch B140408). These electrodes consisted of highly doped diamond deposited on silicon.

Electrode B140408(1) was tested as on leaving the reactor, electrode B140408(2) was tested after activation in an aqueous sodium perchlorate solution and electrode B140408(7) was tested after activation in an aqueous lithium perchlorate solution.

This activation consisted in carrying out twenty redox cycles in an aqueous solution containing a non-electroactive salt, namely lithium perchlorate ($[LiClO_4]$=0.5M; redox activation 2) or sodium perchlorate ($[NaClO_4]$=0.5M; redox activation 1) between the solvent decomposition boundaries, adjusted so that the anodic and cathodic current densities never exceed 150 μA/cm² so as not to degrade the electrode and at the scan rate of 100 mV/s.

Figure 12:
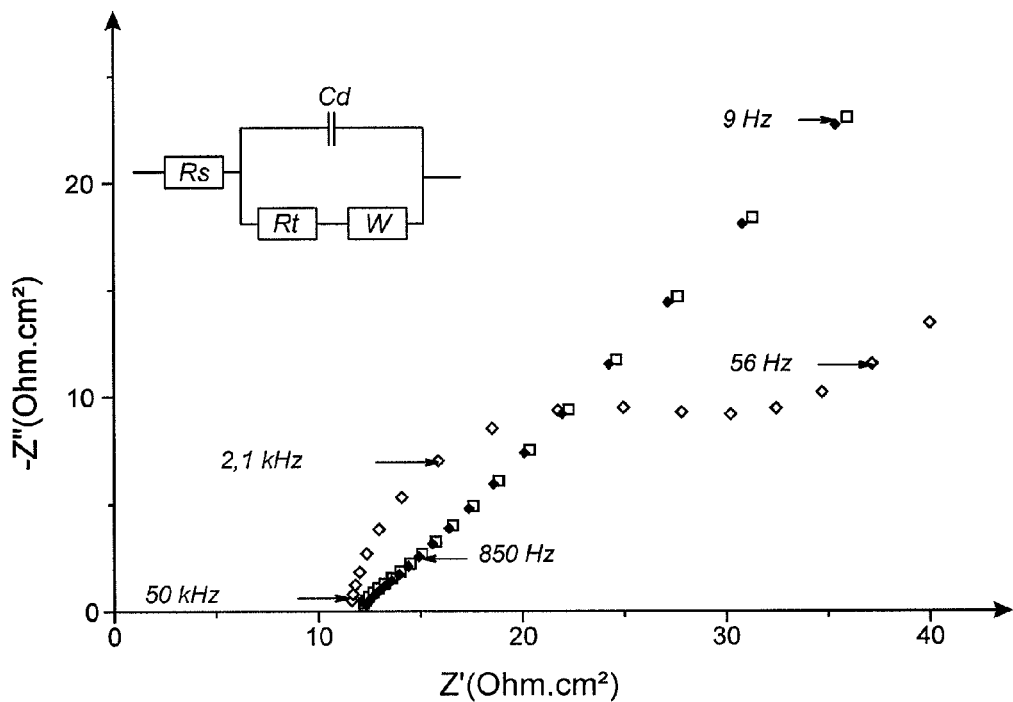
FIG. 12 shows the electrochemical impedance spectroscopy (EIS) of electrode ◇B140408(1) as on leaving the reactor, electrode ☐B140408(2) after redox activation 1 and electrode ◆B140408(7) after redox activation 2. These three electrodes come from the same batch of identical diamond specimens, namely batch B140408.

The impedance spectroscopy (FIG. 12) carried out in an aqueous $[Fe(CN)_6]^{3-/4-}$ ($10^{-3}$M) solution containing a base salt in macroconcentration ($[KCl]$=0.5M), showed that the initial electron transfer resistance ($R_t$=17 Ω/cm²) is very greatly reduced by redox activation 1 ($R_t$=1.2 Ω/cm²) and even more reduced by redox activation 2 ($R_t$=0.94 Ω/cm²) leading to a very substantial increase in the electron transfer rate constant from initially $k_0$=1.6×$10^{-2}$ cm/s to $k_0$=0.22 cm/s after the treatment 1 to $k_0$=0.28 cm/s after treatment 2.

IV.2. XPS Analysis After Redox Activation

After their respective redox activation treatments, electrodes B140408(2) and 3140408(7) were tested by impedance spectroscopy. The measurements were carried out in an aqueous $[Fe(CN)_6]^{3-/4-}$ ($10^{-3}$M) solution containing a base salt in macroconcentration ($[KCl]$=0.5M) at regular time intervals over a period of more than eight hours, which represents more than 30 successive EIS experiments.

Figure 13:
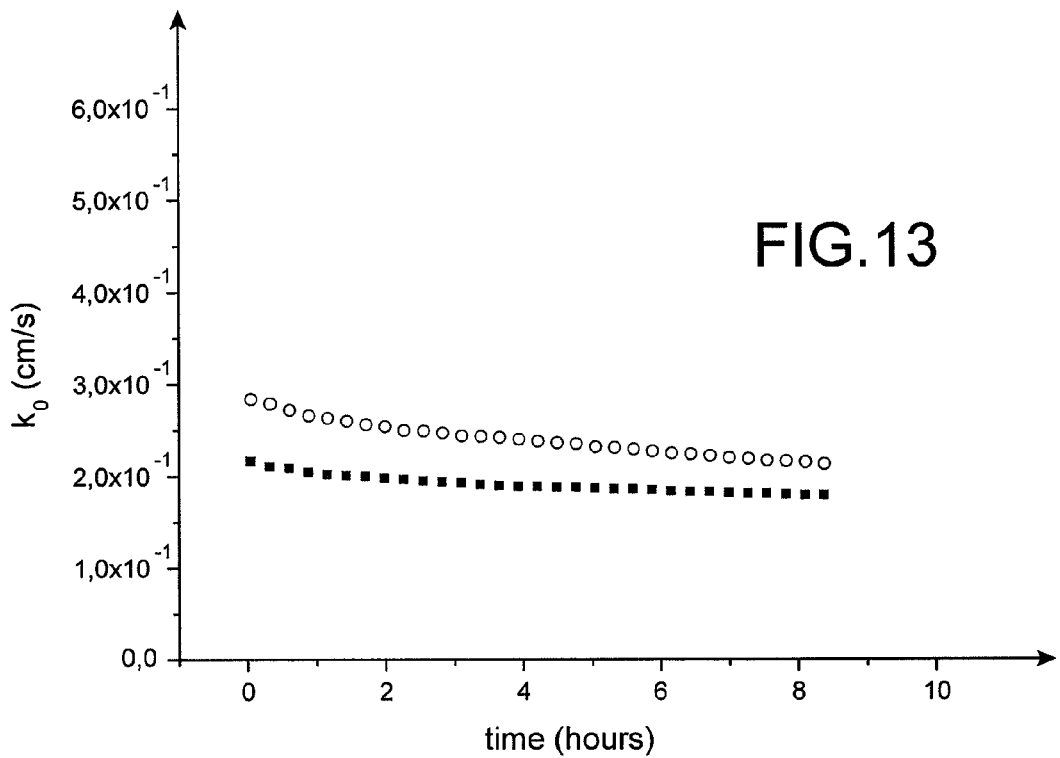
FIG. 13 shows the variation in $k_0$ (in cm/s) of electrode B140408(2) after redox activation 1 and electrode B140408 (7) after redox activation 2 during more than 30 successive EIS experiments carried out over a total time of more than 8 hours.

After these eight hours, electrode B140408(2) retained 83% of its reactivity measured after activation, whereas electrode B140408(7) retained 70% (FIG. 13).

V. Electrode B180707

Electrode B180707 consisted of a highly doped diamond film deposited on a silicon substrate.

Figure 14:
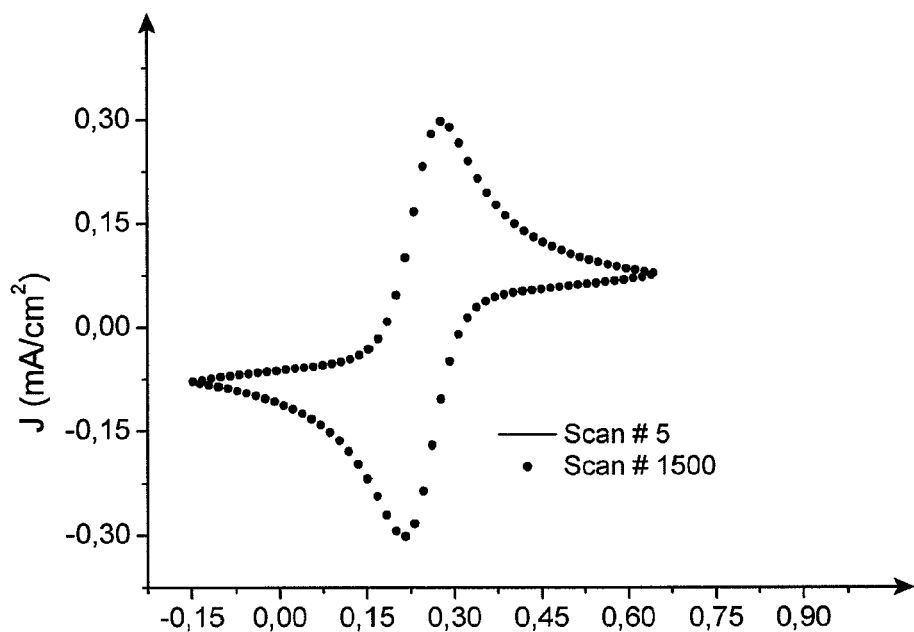
FIG. 14 shows the cyclic voltammetry of electrode B180707.

The cyclic voltammetry curves for this electrode, carried out in an aqueous $[Fe(CN)_6]^{3-/4-}$ ($10^{-3}$M) solution containing a base salt in macroconcentration ($[KCl]$=0.5M), before and after 1500 redox cycles between −0.15 mV and +0.65 mV with respect to Ag/AgCl at a rate of 75 mV/s are shown in FIG. 14.

The two figures merge, thus attesting to the perfect stability of the electrochemical response of the electrode determined by cyclic voltammetry over a period of more than 15 hours.

The potential difference between anodic peak and cathodic peak ($\Delta E_p$=64 mV) also testifies to the very great reactivity of this electrode.

VI. Electrodes B310807(X)

Electrodes B310807(X) were obtained from a batch of identical diamond specimens (batch B310807). These electrodes consisted of highly doped diamond deposited on silicon.

They were tested after activation in an aqueous lithium perchlorate solution. This activation consisted in carrying out twenty redox cycles in an aqueous solution containing a non-electroactive salt, namely lithium perchlorate ([LiClO$_4$]= 0.5M) between the decomposition boundaries of the solvent, adjusted so that the anodic and cathodic current densities never exceeded 150 μA/cm$^2$ so as not to degrade the electrode, at the scan rate of 100 mV/s.

Figure 15:
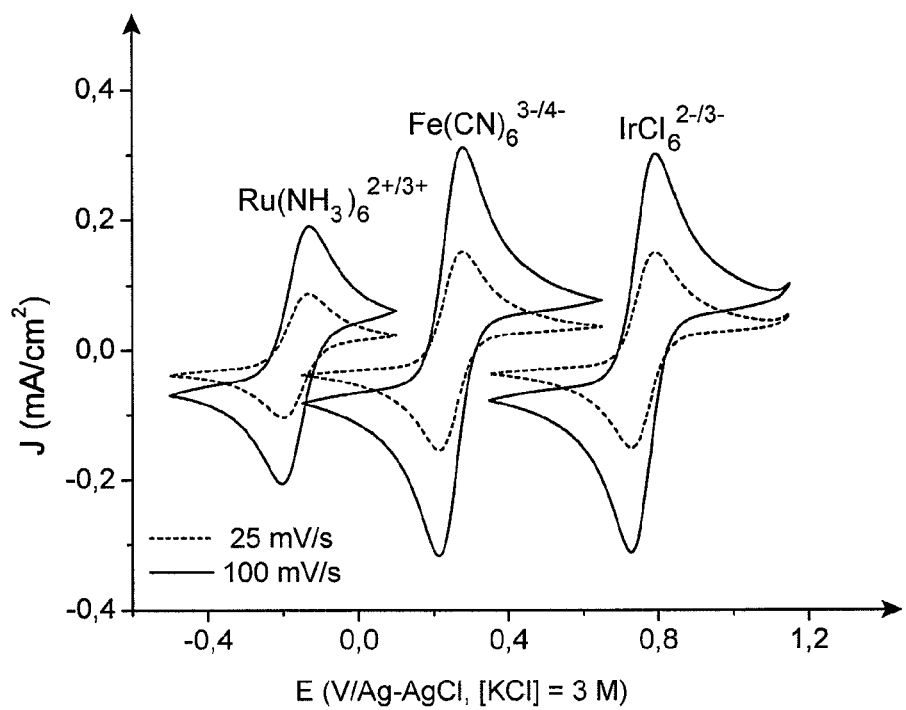
FIG. 15 shows the cyclic voltammograms of electrodes 310807(1), (4) and (9) coming from the same batch of identical specimens after their redox activation.

One of the advantages of diamond is the very wide window of electrochemical potentials that can be achieved thanks to this material. We have therefore desired to explore a part of this window by testing our electrodes with redox couples ([redox couple]=10$^{-3}$M) chosen for their standard electrochemical potential: [Ru(NH$_3$)$_6$]$^{2+/3+}$, [Fe(CN)$_6$]$^{3-/4-}$ (E°=0.3610 V) and [IrCl$_6$]$^{2-/3-}$ (E°=0.867 V). FIG. 15 shows the voltammograms thus obtained.

The activated electrodes show very good reactivity for each of the three redox couples (ΔEp [Ru(NH$_3$)$_6$]$^{2+/3+}$=67 mV, ΔEp [Fe(CN)$_6$]$^{3-/4-}$=64 mV, ΔEp [IrCl$_6$]$^{2-/3-}$=64 mV, scan rate 25 mV/s), thus confirming that the activated diamond electrodes can be used over a wide range of potentials with advantageous charge transfer rates for applications in electrochemistry.

BIBLIOGRAPHY

D. Becker and K. Jüttner, *Electrochimica Acta*, (2003), 49, pp 29-39.
D. Becker and K. Jüttner, *Journal of Applied Electrochemistry*, (2007), 37, pp 27-32.
S. Ferro and A. De Battisti, *Physical Chemistry Chemical Physics*, (2002), 4, pp 1915-1920.
H. Girard, N. Simon, D. Ballutaud, M. Herlem and A. Etcheberry, *Diamond and Related Materials*, (2007), 16, pp 316-325.
C. H. Goeting, F. Marken, A. Gutierrez-Sosa, R. G. Compton and J. S. Foord, *Diamond and Related Materials*, (2000), 9, pp 390-396.
M. C. Granger and G. M. Swain, *The Electrochemical Society*, (1999), 146, pp 4551-4558.
M. Hupert, A. Muck, J. Wang, J. Stotter, Z. Cvackova, S. Haymond, Y. Show and G. M. Swain, *Diamond and Related Materials*, (2003) 12, pp 1940-1949.
D. A. Tryk, K. Tsunozaki, T. N. Rao and A. Fujishima, *Diamond and related material* (2001) 10, pp 1804-1809.
I. Yagi, H. Notsu, T. Kondo, D. A. Tryk and A. Fujishima, *Journal of Electroanalytical Chemistry*, (1999), 473, pp 173-178.

The invention claimed is:

1. A method for activating or for restoring electrochemical reactivity of a diamond-based electrode, comprising:
    subjecting, in the presence of an aqueous solution containing an ionic electrolyte, said electrode to at least one cycle of an alternately cathodic and anodic polarization potential; and
    increasing an amplitude of said potential from an equilibrium potential so as to obtain an anodic and cathodic current density of between 10 μA/cm$^2$ and 1 mA/cm$^2$.

2. The method according to claim 1,
    wherein said diamond-based electrode consists only of monocrystalline diamond, macrocrystalline diamond, microcrystalline diamond, nanocrystalline diamond or ultrananocrystalline diamond (UNCD).

3. The method according to claim 1,
    wherein a portion of said diamond-based electrode comprises monocrystalline diamond-, macrocrystalline diamond-, microcrystalline diamond-, nanocrystalline diamond- or ultrananocrystalline diamond (UNCD).

4. The method according to claim 1, wherein said diamond-based electrode comprises at least one diamond doped by a dopant.

5. The method according to claim 4, wherein said dopant is chosen from the group consisting of boron, nitrogen, phosphorus, nickel, and sulphur and mixtures thereof.

6. The method according to claim 1, wherein said ionic electrolyte is a non-electroactive ionic electrolyte.

7. The method according to claim 6, wherein said non-electroactive ionic electrolyte is a non-electroactive salt chosen from the group consisting of LiClO$_4$, NaClO$_4$, KClO$_4$, Na$_2$SO$_4$, K$_2$SO$_4$, and Li$_2$SO$_4$.

8. The method according to claim 1, wherein said aqueous solution containing an ionic electrolyte is deaerated before said step of subjecting.

9. The method according to claim 1, wherein a first potential to which the diamond-based electrode is subjected is a cathodic polarization potential.

10. The method according to claim 1,
    wherein the step of increasing the amplitude of the potential to which the diamond-based electrode is subjected comprises increasing the amplitude of the potential in increments of between 50 mV and 150 mV.

11. The method according to claim 1, wherein said method further comprises:
    a subsequent step of subjecting, when a desired anodic and cathodic current density is reached, said electrode to at least one alternately cathodic and anodic polarization potential cycle of constant amplitude.

12. The method according to claim 1,
    wherein a final potential to which said electrode is subjected is an anodic polarization potential which reaches the equilibrium potential (OCP).

13. The method according to claim 1,
    wherein the rate at which cathodic polarization and anodic polarization for each potential is carried out is between 50 and 150 mV/s.

14. The method according to claim 1,
    wherein the method is implemented using a three-electrode arrangement having a reference electrode, a working electrode which corresponds to said diamond-based electrode, and a counterelectrode.

\* \* \* \* \*